United States Patent [19]

Pakulis

[11] 4,131,845
[45] Dec. 26, 1978

[54] MICROWAVE MOISTURE SENSOR CHUTE
[75] Inventor: Ivars E. Pakulis, Norridge, Ill.
[73] Assignee: Kay-Ray, Inc., Arlington Heights, Ill.
[21] Appl. No.: 838,505
[22] Filed: Oct. 3, 1977
[51] Int. Cl.² .......................................... G01R 27/04
[52] U.S. Cl. .............................. 324/58.5 A; 343/18 A
[58] Field of Search ........... 324/58.5 A, 58 A, 58.5 B, 324/58 B; 343/703, 18 A

[56] References Cited
U.S. PATENT DOCUMENTS

| | | | |
|---|---|---|---|
| 2,426,820 | 9/1947 | Evans et al. | 343/18 A |
| 2,977,591 | 3/1961 | Tanner | 324/58 B |
| 3,156,917 | 11/1964 | Parmeggiani | 343/18 A |
| 3,187,331 | 6/1965 | Beller | 343/18 A |
| 3,273,150 | 9/1966 | Emerson | 343/18 A |
| 3,308,463 | 3/1967 | Emerson | 343/18 A |
| 3,349,396 | 10/1967 | Reed | 343/18 A |
| 3,460,030 | 8/1969 | Brunton et al. | 324/58.5 A |
| 3,509,568 | 4/1970 | Manning et al. | 343/18 A |
| 3,806,943 | 4/1974 | Holloway | 343/703 |
| 3,818,333 | 6/1974 | Walker | 324/58.5 A |

FOREIGN PATENT DOCUMENTS 253186  11/1970  U.S.S.R. .............................. 324/58.5 A

Primary Examiner—Stanley T. Krawczewicz
Attorney, Agent, or Firm—Alexander D. Ricci; Steven H. Markowitz

[57] ABSTRACT

The present invention is directed to a moisture measuring apparatus which comprises a chute means of a given length for receiving moisture containing material, the chute means having window opening means through which microwaves are transmitted. The transmitter means are aligned with first of said window opening means for transmitting microwaves into said material and the microwaves are attenuated by the moisture contained in said material. Receiver means are aligned with second of said window opening means for receiving at least part of the microwaves. The inside of the chute means is lined with microwave absorbent material to reduce microwave reflections in the inside of the chute means.

24 Claims, 4 Drawing Figures

MICROWAVE MOISTURE SENSOR CHUTE

BACKGROUND OF THE INVENTION

The present invention relates generally to moisture measuring apparatus, and more specifically to such apparatus in which moisture containing material is confined to flow through a chute wherein the moisture content of the material is determined in a non-destructive manner using microwaves.

It is well known in the art that the moisture contained in a product can be determined by utilizing microwaves which when propagated through the product will be attenuated to an extent which is dependent on the quantity of moisture in the product. This attenuation of microwaves is then converted into water density units. It is also known that if this microwave "bombardment" of the product is combined with nuclear energy (e.g., gamma rays) "bombardment" thereof, a direct percent moisture measurement of the product is obtainable. The attenuation of nuclear energy is proportional to the mass of the material between a nuclear energy source and detector, such that in an enclosed space, such as a chute, completely filled with the product, the attenuation can be converted to density (mass/unit volume). By directing the microwaves and nuclear energy through the same cross-section of the product, the water density can be divided by the mass density to give the direct percent moisture measurement. That such methods for measuring moisture content are well known is evidenced by U.S. Pat. No. 3,460,030 which is hereby incorporated by reference to the extent necessary to complete this disclosure.

The use of microwaves to measure moisture content, however, has inherent problems. For example, when the microwave beam is directed perpendicularly to a product as it moves between microwave transmitter and receiver horns, microwaves are reflected between the horns, causing standing wave patterns and resulting in inaccurate moisture measurements. Also for example, a portion of microwaves in the product will be "scattered" so as to miss the receiving horn, likewise resulting in inaccuracies. When the product is confined in a chute, additional accuracy problems arise from microwaves travelling axially along the chute.

In U.S. Pat. No. 3,818,333 to *Walker* various modifications to a conventional chute and microwave antenna system are proposed for overcoming the noted inherent problems related to microwave moisture measurements. According to that reference, the walls of the chute are sloped to avoid microwave reflections from the chute walls into the microwave antennas. To prevent refraction of microwaves passing through the microwave antenna windows, the windows have flat end portions which are mutually parallel. This arrangement of the windows also prevents transmissions of microwaves along the walls of the chute. Since the chute walls are sloped, the windows naturally extend into the chute. So that microwave reflections from the inner and outer surfaces of the windows will cancel each other out, the end portions thereof have uniform thicknesses equal to one-half the wavelength of the microwaves. Since the antenna housings are connected to the walls of the chute, microwave absorbent material surrounds the antennas apparently to prevent the launching of surface microwaves into the chute via the connections between the housings and walls. Finally, to prevent reflection of microwaves through the windows from the antenna housing portions located directly behind the antennas, those housing portions are lined with microwave absorbent material.

DESCRIPTION OF THE INVENTION

According to the present inventive apparatus, the above-noted problems related to performing microwave moisture measurements are significantly reduced or eliminated by means which are simple and relatively economical, particularly as compared to *Walker*. By simply lining the inside walls of the chute with microwave absorbent material, microwave reflections in the inside area of the chute are reduced or eliminated, so that accurate moisture measurements are obtainable for a product flowing therethrough. The absorbent liner is, in turn, lined with protective liner to prevent cross-contamination between the product and the absorbent liner. By providing window openings in the walls of the chute, cutting away the absorbent liner at said openings, and extending the protective liner across the same, the protective liner also serves as the microwave windows. Accordingly, by providing substantially parallel chute walls, these flat microwave windows will not interfere with the flow of product through the chute. Also, using the apparatus according to the present invention, accurate moisture measurements are achievable for a "dynamic" product, that is one which is continuously flowing past the measuring transmitters and receivers. By also providing a penetrating ray (e.g., gamma ray) transmitter and receiver arrangement, the density of the product is also measurable. By directing the penetrating rays and microwaves through the same cross-section of the product, the resulting density and moisture content measurements can be fed to a percent moisture determining means wherein the moisture measurement is divided by the density measurement and read-out of percent moisture content is provided.

These and other objects, features and advantages of the present invention will become more apparent from the following detailed description when taken in connection with the accompanying drawing which shows, for purposes of illustration only, several views and embodiments in accordance with the present invention, and wherein.

Figure 1:
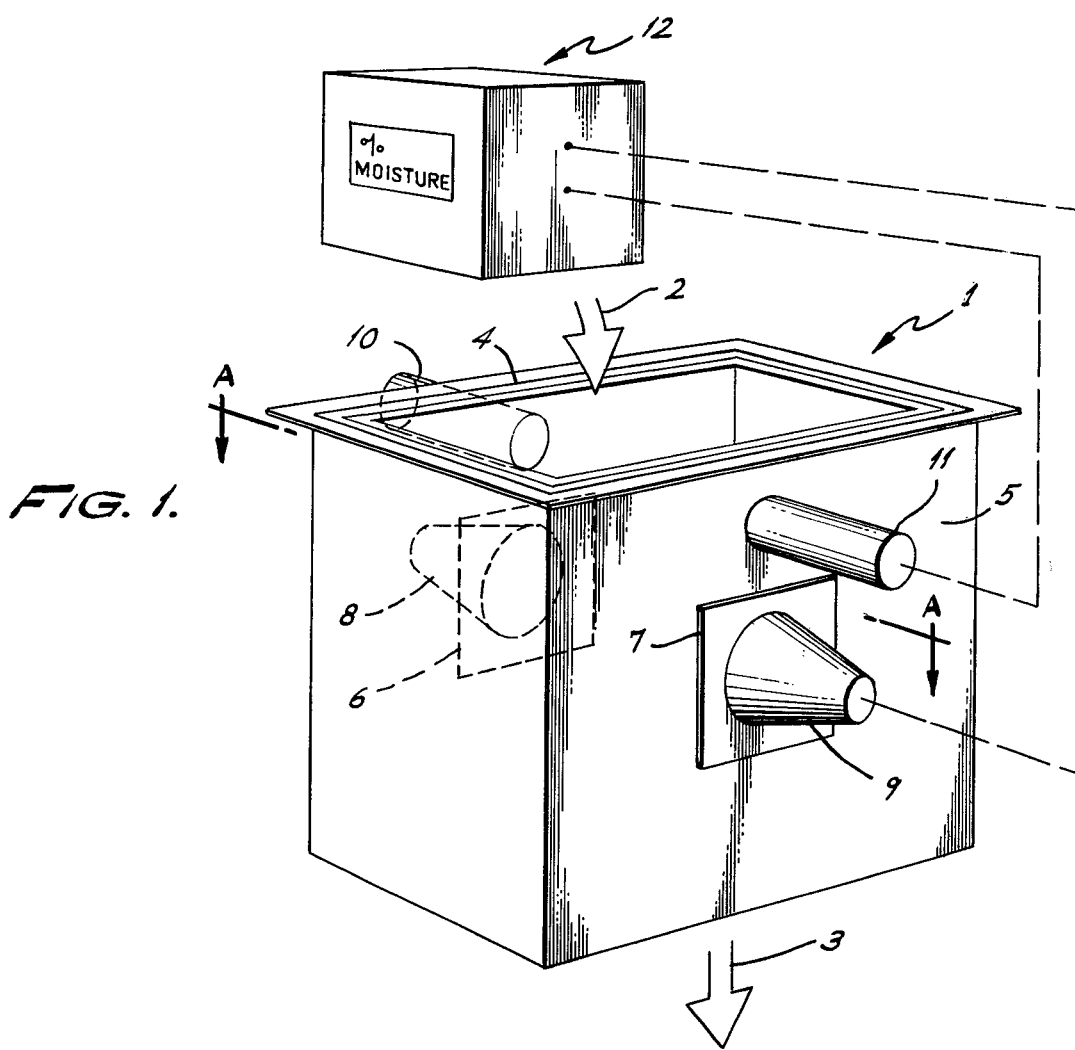
FIG. 1 is a perspective schematic view of a microwave moisture sensor chute in accordance with the present invention.
Figure 2:
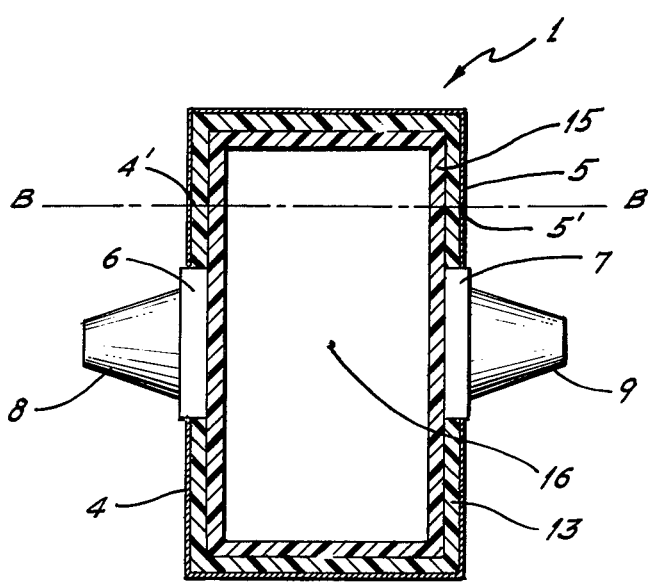
FIG. 2 is a cross-sectional plan view of the chute taken along line A—A shown in FIG. 1.

Referring now to the drawing wherein like reference numerals are used throughout to designate like parts, and more particularly to FIGS. 1 and 2, chute 1 is provided through which moisture containing material flows as generally indicated by arrows 2 and 3. Provided in facing wall sections 4 and 5 of the chute are microwave window openings 6 and 7. To prevent interference with the flow of moisture containing material through the chute, walls 4 and 5 are preferably mutually parallel in the axial direction of the chute in that opposing surfaces 4', 5' thereof along an axial plane BB (FIG. 2) parallel to the chute axis 16 are parallel. In alignment with these window openings and located along the outside of the chute are microwave transmitter means 8 and microwave receiver means 9, preferably microwave horns. The horns can be arranged substantially perpendicularly to their corresponding wall section. Also provided are penetrating ray transmitter means 10 and penetrating ray receiver means 11. For simplicity in design and convenience of use, they are provided in the same walls as the microwave horns. Gamma rays are preferred as a penetrating ray and, accordingly, reference will hereinafter be made to such rays in describing the invention. The gamma ray transmitter 10 and microwave transmitter are preferably arranged to transmit energy substantially through the same cross-section of the chute, and therefore, generally through the same cross-section of moisture containing material passing through chute 1. The gamma rays detected at receiver 11 and the microwaves detected at receiver 9 are converted into signals representative of the mass density and water density, respectively; and these signals are transmitted to percent moisture determining means 12 of any well known construction, such as a multiplier/divider module and read-out device wherein they are converted to a percent moisture determination.

With particular reference to FIG. 2, to reduce the various known microwave reflections along the inside area of chute 1, the inside of the chute is lined with microwave absorbent material 13, such as Eccosorb brand foams sold by Emerson & Cuming, Inc. The absorbent is cut out at window openings 6 and 7 so as not to interfere with transmissions of microwaves between the horns 8 and 9. It is preferred that the chute is lined with absorbent 13 substantially along its entire axial length. The amount (length) of absorbent required to effectively reduce microwave reflections inside the chute will vary as the frequency of the horn varies. Specifically, as the frequency of the microwaves increases, the amount of absorbent required decreases. As is well known, the smaller horns (8.2 to 12.4 Gigahertz frequency) have higher frequencies and are more sensitive to water. Accordingly, the smaller horns can't be used for high bulk density materials with high moisture contents. The larger horns (3.95 to 5.85 Gigahertz frequency) have small frequencies and are less sensitive to water. These larger horns are particularly well suited for use with high bulk density, high moisture content materials. There apparently is no simple formula available for easy determination of the required absorbent length for a given horn. However, the present inventors did determine by experimentation that for a 5.8 Gigahertz microwave horn, 30 inches of absorbent is the required length. Accordingly, the present inventors contemplate as the best mode for determining the required absorbent length for higher frequency horns a simple test as follows:

1. A 30 inch open-ended empty chute fully lined with absorbent and having a microwave horn arrangement as in FIG. 1 should be used.

Figure 3:
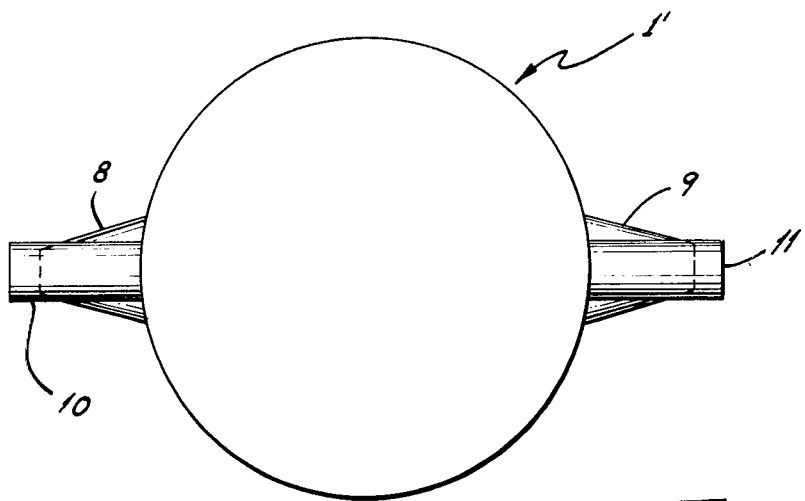
FIG. 3 is a partial plan view of a modified embodiment of a chute in accordance with the present invention.

2. While operating the horns, a simple rod 14 having a flat metal plate at one end should be inserted in one end of the chute as shown in FIG. 3.

3. As the rod is moved downwardly toward the horns, the output from the receiving horn 9 is observed.

4. At that point at which the output from horn 9 begins to change, the required absorbent length has just been passed. Of course, the change in the output from the receiving horn is caused by microwaves from transmitter horn 8 which are reflected by the rod 14 inside the chute and are not absorbed by the absorbent 13.

This noted test was the one used to determine the 30 inch required length for the 5.8 Gigahertz horn. Suitable results have been obtained using ¼ inch thick low density open cell Eccosorb foam as absorbent 13. Of course, for lower frequency horns, the same test could be used but with a longer chute.

Referring again particularly to FIG. 2, to prevent direct contact between the moisture containing material travelling through the chute and microwave absorbent 13, the inside surface of the absorbent is lined with protective liner 15. Unlike absorbent 13, the protective liner extends across microwave window openings 6 and 7 to serve as microwave windows. So as not to interfere with the flow of material through the chute, the liner lies "flat" across the openings, that is, it does not protrude into the chute. Sheets of "Lexan" polycarbonate liner material of 0.060 inch thickness which are heat formed and bonded have proven to be useful as the protective liner.

Figure 4:
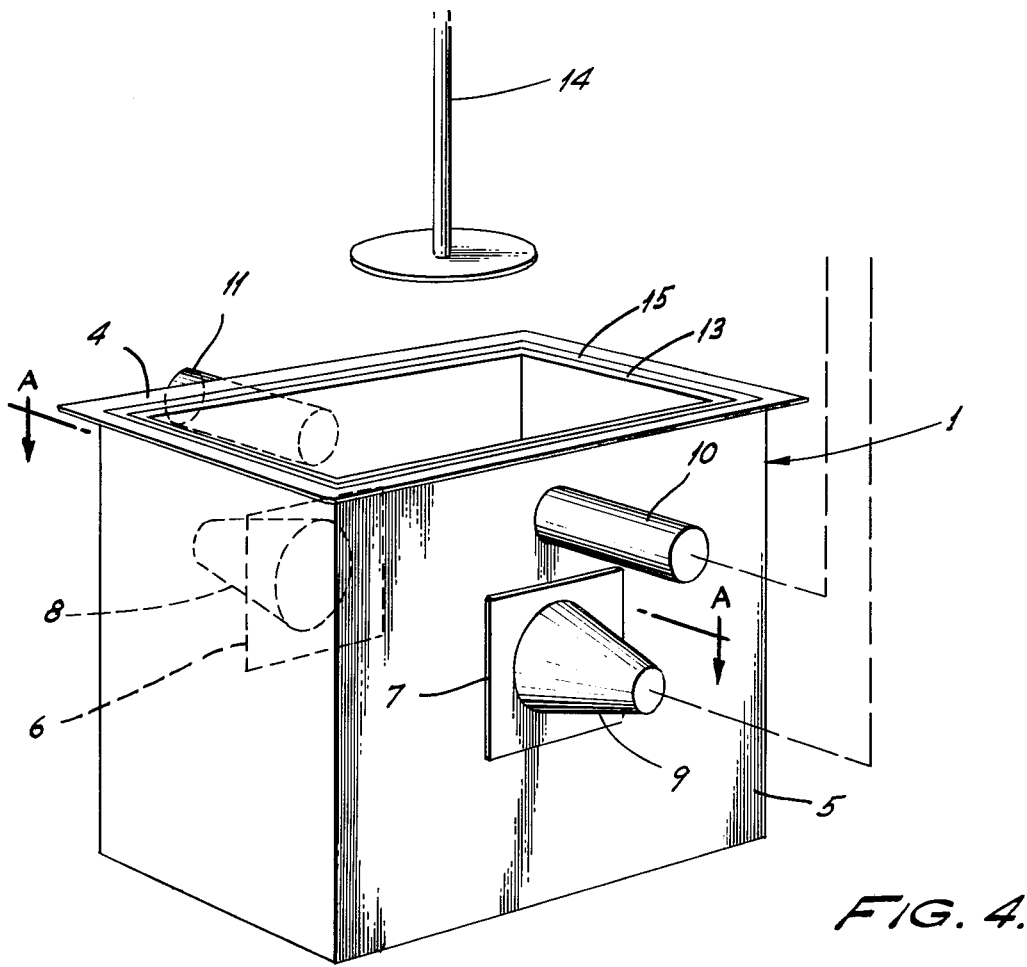
FIG. 4 is a perspective view as in FIG. 1 but illustrating a test method utilized in practicing the present invention.

In FIG. 4, a chute 1' of circular cross-section is illustrated with microwave horns 8 and 9, gamma ray transmitter 10 and gamma ray receiver 11 arranged thereon.

Having thus described the invention, what is claimed is:

1. Moisture measuring apparatus comprising
   chute means of a given length for receiving moisture containing material, said chute means having walls with window opening means through which microwaves are transmitted,
   transmitter means aligned with first of said window opening means for transmitting microwaves into said material such that said microwaves are attenuated by the moisture contained in said material, and
   receiver means aligned with second of said window opening means for receiving at least part of said microwaves transmitted by said transmitter means,
   wherein the walls of said chute means are all lined along an inside surface thereof with microwave absorbent material to reduce microwave reflections in the inside area of the chute means,
   wherein said microwave absorbent material is lined along its inside surface with protective liner to prevent direct contact between the microwave absorbent material and moisture containing material travelling through the chute,
   wherein each of said microwave window opening means is provided with flat microwave window means, and
   wherein said walls are mutually parallel in the axial direction of said chute means.

2. The apparatus of claim 1, wherein said protective liner is permeable to microwaves.

3. The apparatus of claim 2, wherein said absorbent material is cut away at each of said window opening means.

4. The apparatus of claim 3, wherein said protective liner extends across said window opening means to provide said microwave window means.

5. The apparatus of claim 4, wherein said transmitter means and said receiver means are located outside of said chute means.

6. The apparatus of claim 4, wherein said transmitter means and said receiver means are facing microwave horns.

7. The apparatus of claim 6, wherein said horns are each disposed along the outside of and substantially prependicularly to a corresponding wall section of said chute means.

8. The apparatus of claim 1, wherein penetrating ray transmitter means for transmitting penetrating rays into said moisture containing material and penetrating ray receiving means for receiving at least a portion of said transmitted penetrating rays are provided to measure the density of said moisture containing material, said penetrating ray transmitter and receiver means being arranged with respect to said chute means to measure the same cross-section of said moisture-containing material as said microwave transmitter and receiver means.

9. The apparatus of claim 4, wherein penetrating ray transmitter means for transmitting penetrating rays into said moisture containing material and penetrating ray receiving means for receiving at least a portion of said transmitted penetrating rays are provided to measure the density of said moisture containing material, said penetrating ray transmitter and receiver means being arranged with respect to said chute means to measure the same cross-section of said moisture-containing material as said microwave transmitter and receiver means.

10. The apparatus of claim 9, wherein said transmitter means and said receiver means are facing microwave horns.

11. The apparatus of claim 10, wherein said horns are each disposed substantially perpendicularly to a corresponding wall section of said chute means.

12. The apparatus of claim 11, further comprising percent moisture determining means which receives a moisture content determination from said microwave receiver horn, receives a density determination from said penetrating ray receiver means and converts the determinations to a percent moisture determination.

13. The apparatus of claim 12 wherein said protective liner is plastic. 12,

14. The apparatus of claim 13, wherein said microwave transmitter means and receiver means are each one microwave horn.

15. The apparatus of claim 14, wherein said chute means is rectangular in shape.

16. The apparatus of claim 14, wherein said chute means is a circular conduit.

17. The apparatus of claim 1, wherein said chute means is lined with said absorbent material substantially along the entire inside length of said chute means.

18. The apparatus of claim 4, wherein said chute means is lined with said absorbent material substantially along the entire inside length of said chute means.

19. The apparatus of claim 14, wherein said chute means is lined with said absorbent material substantially along the entire inside length of said chute means.

20. The apparatus of claim 17, wherein said protective liner covers substantially the entire inside surface of said absorbent liner.

21. The apparatus of claim 18, wherein said protective liner covers substantially the entire inside surface of said absorbent liner.

22. The apparatus of claim 19, wherein said protective liner covers substantially the entire inside surface of said absorbent liner.

23. The apparatus of claim 13, wherein said penetrating rays are gamma rays.

24. Apparatus for measuring the percent moisture content of moisture containing material comprising:
sidewalls arranged to define a chute through which moisture containing material flows in an axial direction thereof,
first and second window openings in opposite corresponding first and second substantially axially parallel sidewalls of said chute, said window openings facing each other across said chute such that said moisture containing material flows therebetween;
microwave transmitter means located outside said first sidewall and aligned with said first window opening to direct microwaves through said first window opening, through said moisture containing material, and through said second window opening;
microwave receiver means located outside said second sidewall and aligned with said second window opening to receive microwaves from said microwave transmitter means,
penetrating ray transmitter means disposed along a sidewall of said chute for transmitting penetrating rays through said moisture containing material, and penetrating ray receiver means disposed along a sidewall of said chute to receive penetrating rays from said penetrating ray transmitter means,
wherein said sidewalls of said chute are all lined along an inside surface thereof with microwave absorbent material,
wherein said microwave absorbent material is cut away at said window openings,
wherein said microwave absorbent material is lined along its inside surface with protective liner,
wherein said protective liner also covers said window openings to provide microwave windows, and
wherein said microwave windows are substantially flat.

* * * * *